United States Patent [19]

Kurtz et al.

[11] 4,312,351
[45] Jan. 26, 1982

[54] DRAINAGE DEVICE WITH SEPARATE OUTFLOW CHAMBER

[76] Inventors: Leonard D. Kurtz, 46 Woodmere Blvd., Woodmere, N.Y. 11598; Robert E. Bidwell, 27 Montrose Pl., Long Island, N.Y. 11746

[21] Appl. No.: 107,329

[22] Filed: Dec. 26, 1979

[51] Int. Cl.³ .............................................. A61M 1/00
[52] U.S. Cl. .................................................... 128/276
[58] Field of Search ....... 128/276, 277, 278, DIG. 24, 128/762, 767; 137/205

[56] References Cited

U.S. PATENT DOCUMENTS

| | | | |
|---|---|---|---|
| 4,015,603 | 4/1977 | Kurtz et al. | 128/276 |
| 4,112,948 | 9/1978 | Kurtz et al. | 128/276 |
| 4,261,362 | 4/1981 | Kurtz et al. | 128/276 |

*Primary Examiner*—Robert W. Michell
*Assistant Examiner*—J. L. Kruter

[57] ABSTRACT

A drainage device is provided with a collection chamber, underwater seal chamber and a separate outflow chamber. The underwater seal chamber which prevents the flow of atmospheric air from the device into the pleural cavity of the patient is formed by a recessed portion in a partition separating the underwater seal chamber from the collection chamber. The passageway from the underwater seal chamber into the collection chamber is disposed centrally of the partition separating the chambers and a baffle is formed around the opening to prevent excessive loss of fluid from the underwater seal chamber into the collection chamber when the device is inadvertently tilted. The outflow chamber is closed off from the collection chamber and is connected with the underwater seal chamber by means of a tubular passageway adjacent the upper wall of the drainage apparatus so as to prevent fluid from passing from the underwater seal chamber into the outlet passageway. A oneway valve is provided in the outlet chamber to prevent backflow of air from the atmosphere into the device but which permits outflow of air from within the device when the air pressure within the device is higher than atmospheric pressure or when the device is used with a suction pump. A hanger attachment is provided to permit the device to stand on the floor or be hooked onto the bedside.

11 Claims, 5 Drawing Figures

DRAINAGE DEVICE WITH SEPARATE OUTFLOW CHAMBER

BACKGROUND OF THE INVENTION

The invention relates to a drainage device and more particularly to a device which is designed to drain fluids from a body cavity such as the pleural cavity and to maintain proper pressures within the body cavity.

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as caused by lung surgery or foreign objects which pierce the ribcage or, for example, where the patient has pleurisy, generates fluids in the pleural cavity which tend to obstruct normal breathing operations. It is necessary to provide a device which can remove these fluids from the pleural cavity and at the same time, ensure that the desired degree of negative pressure is maintained within the pleural cavity.

One of the basic types of apparatus which has been used for this purpose is shown, for example, in U.S. Pat. Nos. 3,363,626 and 3,363,627. This apparatus is known as an underwater drainage apparatus and provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity. However, such an apparatus required prefilling the underwater seal chamber with water and also prefilling the pressure manometer chamber to the desired level to maintain the desired degree of negativity within the pleural cavity. However, there has been a need for a drainage device which could be attached to the patient's pleural cavity and which did not require any prefilling, and which did not require a vacuum pump. For example, in emergency situations in the field where liquid may not be available for filling the underwater seal and manometer chambers or where a vacuum pump may not be available, it is necessary to provide a device which can be attached to a patient's pleural cavity to permit drainage of fluids to allow the lungs to expand.

The drainage system disclosed in U.S. Pat. No. 4,015,603 provided an apparatus which eliminated the need for a prefilled underwater seal chamber by locating the underwater seal at the lower end of the thoracotomy tube at the upper end of the drainage device. In the device shown in this prior patent, the underwater seal was formed by liquid drained from the patient's pleural cavity. However, the device disclosed in U.S. Pat. No. 4,015,603 required the use of a self-regulated vacuum pump and, in situations where such a pump was not available, the device shown in this prior art patent could not be utilized.

Furthermore, the location of the underwater seal chamber at the lower end of the thoracotomy tube as disclosed in U.S. Pat. No. 4,015,603 created a further problem in certain unusual circumstances. In case of a patient having a blockage in the bronchial tubes, such that the patient was having severe problems in getting air into the lungs, exceedingly high negativity was being created in the pleural cavity. Such high negativity caused the fluid in the underwater seal to be drawn upwardly through the thoracotomy tube and, if the degree of negativity was sufficiently high, it was possible for fluid to reenter the pleural cavity. This condition of fluid from the underwater seal chamber reentering the pleural cavity could cause infection or otherwise create problems for the patient. In addition, it was possible to entirely lose the seal provided by the underwater seal chamber during periods of high negativity in the pleural cavity. The loss of the water seal has the potential for serious damage in the event the suction becomes disconnected or the device is used as a two bottle system with the collection chamber open to atmosphere.

In U.S. Pat. No. 3,853,128 there is disclosed a positive pressure relief valve in a drainage apparatus having a conventional underwater seal and manometer chamber. The positive pressure relief valve is disposed between the underwater seal and manometer chambers and provides relief from high pressure surges within the collection chamber. The device disclosed in U.S. Pat. No. 3,853,128 must, however, be prefilled prior to use and does not function as a two chambered device which is usable without prefilling.

SUMMARY OF THE INVENTION

According to the invention, a drainage device is provided which overcomes many of the above mentioned problems in connection with prior art drainage devices. One aspect of the invention concerns the provision of a drainage device wherein an underwater seal chamber is formed by a partition which extends partially across the collection chamber with a tube extending downwardly from the inlet into a recess formed in this partition to provide the underwater seal. A oneway valve is provided in the fluid passageway to the outlet from the collection chamber with the oneway valve permitting gases to flow outwardly from the collection chamber but which prevents the inflow of gases from the outlet to the collection chamber.

The underwater drainage apparatus of the invention does not require prefilling with water, does not require a vacuum pump, but has provisions for attaching a vacuum pump thereto. The apparatus includes an underwater seal chamber that maintains the seal even when the drainage device is inadvertently tilted. The present invention also provides further means for maintaining a water seal when the device is used as a two bottle system with the collection chamber thereof open to atmosphere.

In a particular embodiment of the present invention, a drainage apparatus is provided having a sloping partition forming the underwater seal chamber above the partition and a collection chamber beneath the partition. Directly beneath the inlet to the drainage apparatus there is disposed a U-shaped recess in the partition that forms an underwater seal with a tube extending downwardly from the inlet.

In another aspect of the present invention, the drainage device comprises a container having an inlet thereto in an upper end thereof and a partition extending along the length of the container, which forms a collection chamber beneath the partition and an underwater seal chamber above the partition. A separate outlet chamber is disposed in the upper end of the container and has an outlet to which a suction hose can be connected to atmosphere. A separate passageway connects the outlet chamber to the underwater seal chamber through a one-way valve that prevents fluid communication back to the underwater seal chamber. The passageway is disposed adjacent the upper end of the container so as to prevent liquid carryover between the underwater seal chamber and the outlet chamber. An opening in the partition permits the flow of fluid from the upper underwater seal chamber to the lower collection chamber and is provided with means to prevent the flow of fluid from the underwater seal chamber into the passageway.

In still another aspect of the present invention, means are provided surrounding the opening in the partition to prevent substantial loss of fluid from the underwater seal chamber into the collection chamber when the container is tipped. There can further be provided a U-shaped recess in the partition between a tube connecting the thoracotomy tube inlet and the underwater seal chamber so as to provide a reservoir of fluid to maintain this seal in the event the drainage device is inadvertently tilted.

Additional features and advantages of the present invention will be apparent from a consideration of the following detailed description of the preferred embodiment of the invention in connection with the accompanying drawings.

DETAILED DESCRIPTION OF THE PREFERRED EMBODIMENT

Figure 1:
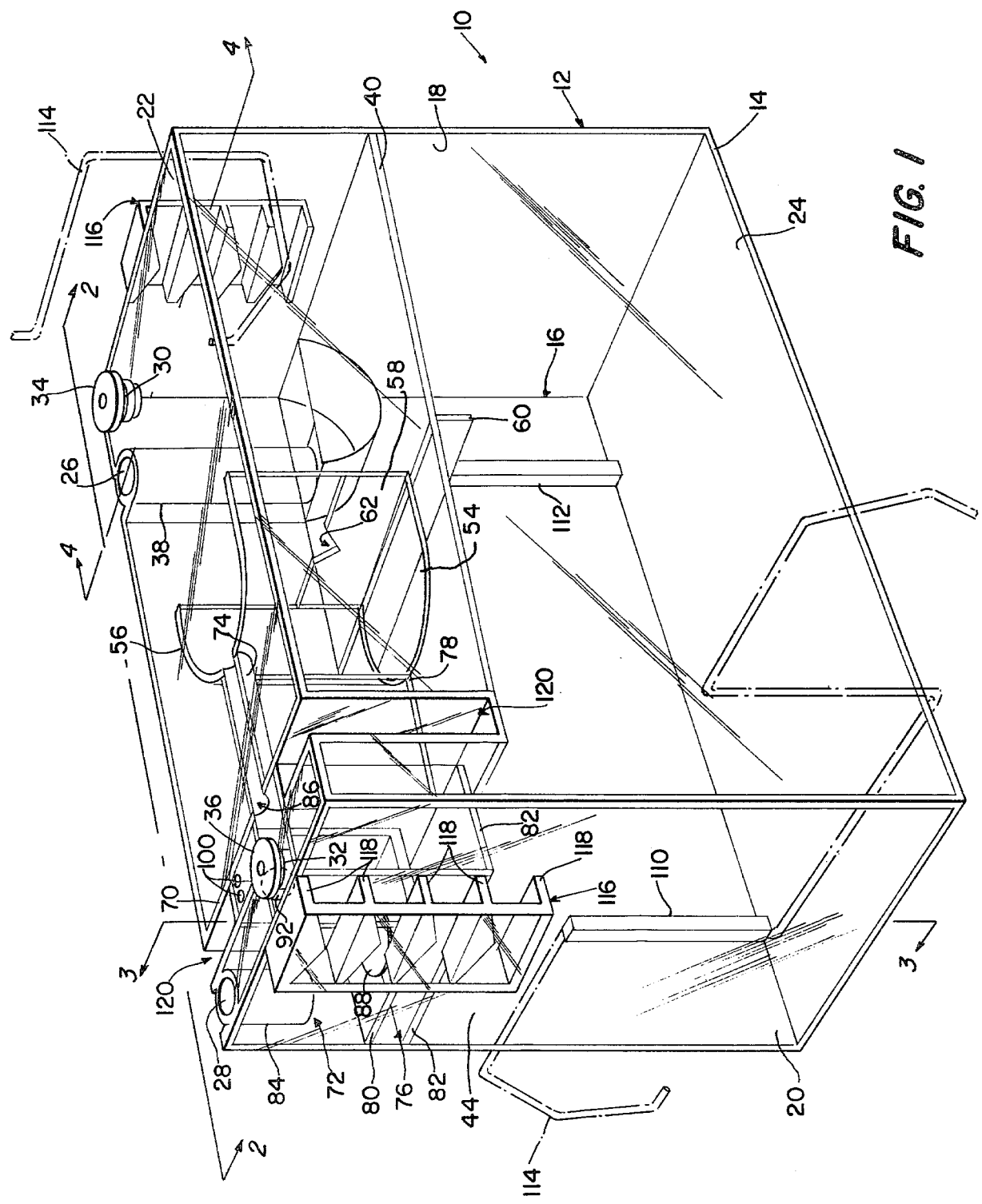
FIG. 1 is a perspective view of the two-chambered underwater drainage device with a separate outflow chamber.

Referring now more specifically to the drawings wherein like numerals are used to represent like elements throughout the several views, there is depicted in FIG. 1 an underwater drainage device 10 that comprises a container 12 which may be formed of a rigid transparent plastic material or the like. Container 12 is depicted in the present embodiment in a substantially box-like shape having four vertical walls when in the upright position, namely a front wall 14, a rear wall 16, a first end wall 18, and a second end wall 20. In addition, container 12 is provided with a top wall 22 and a bottom wall 24.

Underwater drainage device 10 is also provided with an inlet 26 for attachment of a thoracotomy tube which extends into the patient's pleural cavity. An outlet 28, described in greater detail hereinbelow, is adapted to connect the container with a source of suction. Container 12 is further provided with a first opening 30 located adjacent to inlet 26 and a second opening 32 located at the same end as outlet 28. Rubber diaphragms 34 and 36, described in greater detail hereinbelow, are respectively disposed in first opening 30 and second opening 32 in sealing engagement with container 12.

Figure 2:
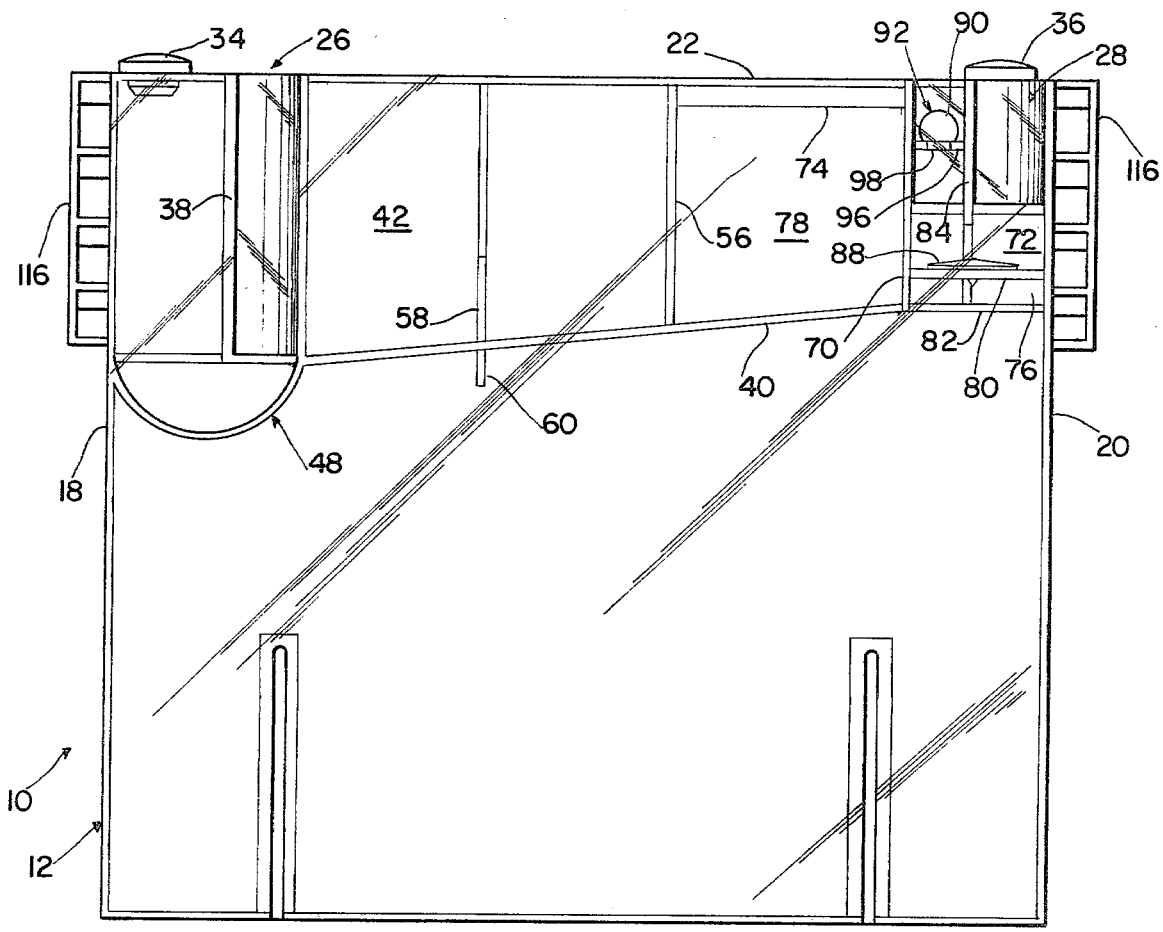
FIG. 2 is a side elevational view of the drainage device taken along line 2—2 of FIG. 1.
Figure 3:
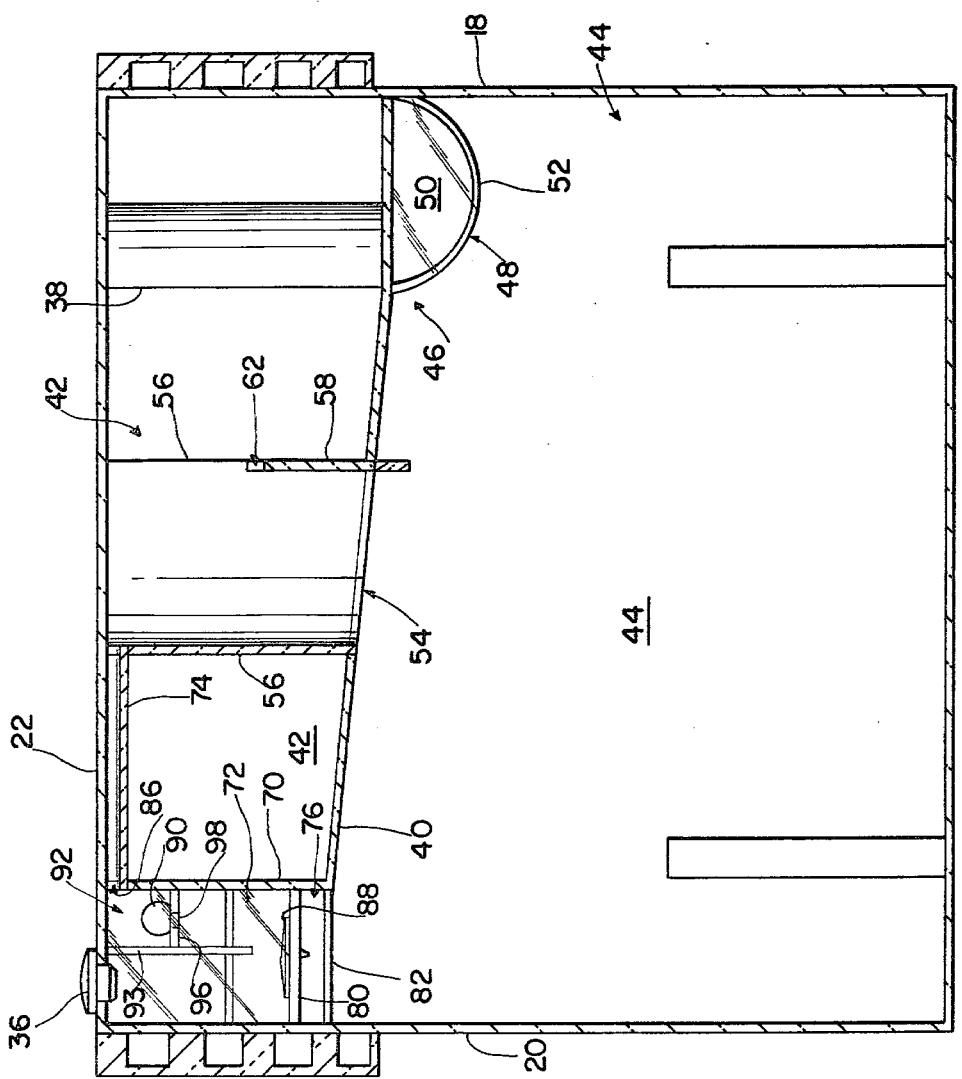
FIG. 3 is a sectional side elevational view along line 3—3 of FIG. 1.

With particular reference to FIGS. 1, 2 and 3, an internal inlet tube 38 extends downwardly from drainage device inlet 26 and terminates at a sloping main partition 40. Main partition 40 extends horizontally from first end wall 18 to second end wall 20 and transversely from front wall 14 to rear wall 16 to divide drainage device 10 into an upper underwater seal chamber 42 and a lower collection chamber 44. One corner of main partition 48, located below inlet tube 38, is provided with a U-shaped recessed portion 46. Recessed portion 46 is defined by a cup portion 48 having a semicircular side 50 attached to a circular bottom 52. The other side of cup portion 48 is formed by rear wall 16.

Cup portion 48 is located and sized so as to satisfy two, somewhat conflicting criteria. The purpose of cup portion 48 is to retain liquid drained from the pleural cavity so that after a predetermined amount of liquid has been drained and the bottom of inlet tube 38 is covered, a seal is automatically formed. Thus, one criterion is that cup portion 48 be small enough so that only a relatively little amount of liquid need be drained from the pleural cavity of the patient before a seal is formed. On the other hand, it is an important feature of the present invention that the seal, once formed, is not destroyed by the inadvertent tilting of drainage device 10. Hence, cup portion 48 should have a sufficiently large enough capacity so that should some liquid be lost therefrom, the seal will not be broken. Obviously, the bottom of inlet tube 38 can extend downwardly into cup portion 48 to aid in preventing the loss of a seal if drainage device 10 becomes tilted. However, this has a disadvantage in that the greater the height of the liquid up inlet tube 38, the greater the differential in pressure will be between the pleural cavity and the seal chamber. Therefore, in a presently preferred embodiment of the present invention, the bottom of inlet tube 38 extends only to the bottom of main partition 40.

As mentioned above, main partition 40 is sloped from second end wall 20 to first end wall 18. Thus, main partition 40 is spaced at a greater distance from top wall 22 adjacent first end wall 18 than at second end wall 20. The sloping of main partition 48 permits the liquid accumulating in seal chamber 42 to flow in the direction of cup portion 48, thereby tending to keep cup portion 48 filled upon a minor tilting of drainage device 10.

Figure 5:
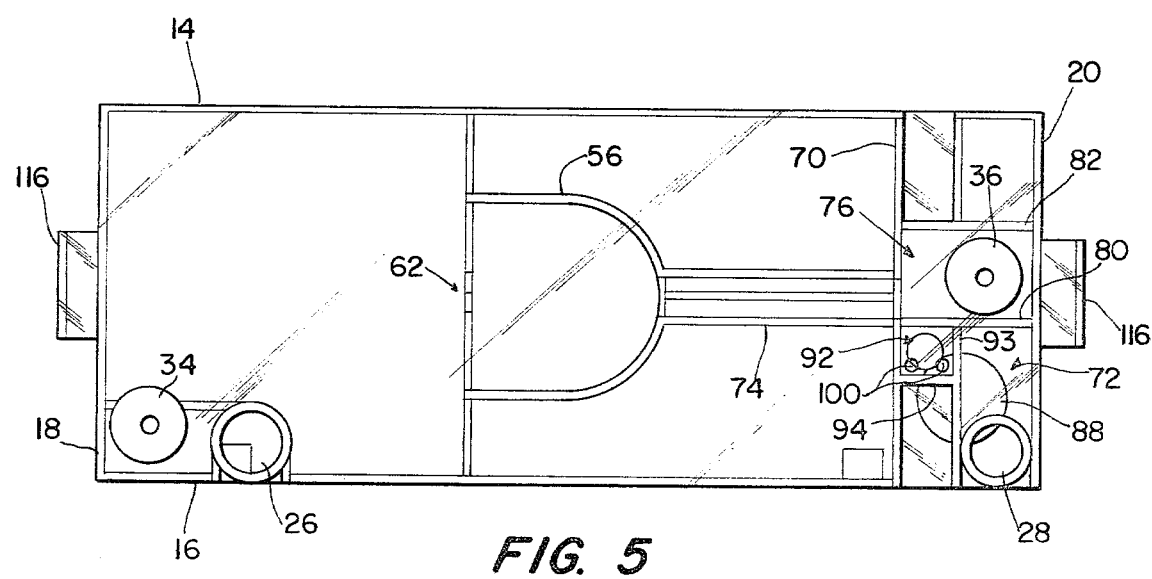
FIG. 5 is a top plan view of the drainage device.
Figure 4:
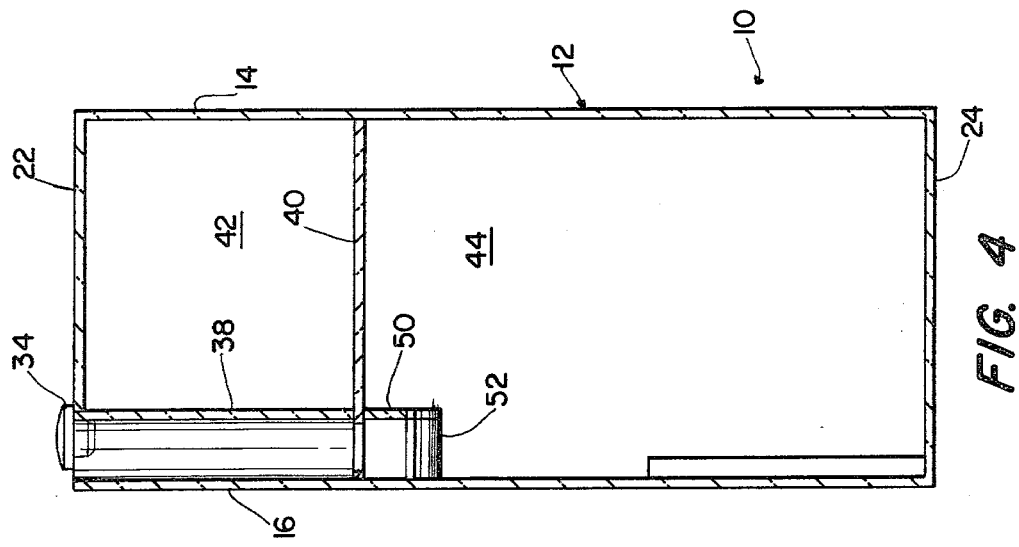
FIG. 4 is a sectional end elevational view along line 4—4 of FIG. 1.

Located substantially centrally in main partition 40 is an opening 54 for permitting the flow of fluid (i.e., both liquid and gas) from underwater seal chamber 42 into collection chamber 44. As shown in FIGS. 1, 2 and 5, means surrounding opening 54 is provided to prevent a substantial loss of liquid from underwater seal chamber 42 into collection chamber 44, should the container be tipped. This means includes a U-shaped baffle 56 that extends between main partition 40 and top wall 22. The open end of baffle 56 faces first end 18 and is aligned substantially parallel therewith. A gate 58 is connected at each end to the open ends of baffle 56, and is also connected at the bottom to main partition 40. Gate 58 extends upwardly a predetermined distance toward top wall 22 such that the depth of the liquid in underwater seal chamber 42, when drainage device 10 is in the normal upright position, is determined by the height of gate 58. Thus, as soon as the liquid drained from the pleural cavity accumulates in underwater seal chamber 42 to a depth greater than the height of gate 58, the extra liquid flows over gate 58 through opening 54 into collection chamber 44 below. A drip ledge 60 is located on the underside of main partition 40 directly below the bottom of gate 58. Drip ledge 60 permits a more efficient flow of the overflow liquid from underwater seal chamber 42 into collection chamber 40. As shown in FIG. 1, a notch 62 can be centrally provided in gate 58 so as to more accurately control the depth of the reservoir liquid in underwater seal chamber 42.

With reference to FIGS. 2 and 5, a vertical partition 70 is located toward one end of main partition 40 and divides seal chamber 42 from an outlet chamber 72. Vertical partition 70 extends transversely from front wall 14 to rear wall 16 and vertically from main partition 40 to top wall 22. Fluid communication is provided between underwater seal chamber 42 and outlet chamber 72 by a tubular passageway 74. One end of tubular passageway 74 is located at the upper, rounded closed end of baffle 56 and runs along the bottom of top wall 30 to connect to outlet chamber 72 through a further, outlet connecting chamber 76, described in greater detail hereinbelow. A vertical plate 78 extends between the bottom of passageway 74 and the top of main partition 40 and runs lengthwise from vertical partition 70 to the closed end of baffle 56. Thus, vertical plate 78 and baffle 56 divide seal chamber into two parts and together prevent the collected liquid from sloshing transversely in seal chamber 42. Two, spaced-apart, L-shaped partitions, an inner partition 80 and an outer partition 82, extend between second end wall 20 and vertical partition 70. The space between partitions 80 and 82 defines connecting chamber 76 and the space between inner partition 80 and the walls of container 12 define outlet chamber 72. Container outlet 28 communicates through an outlet tube 84 with the top of outlet chamber 72 and second opening 32 communicates with the top of connecting chamber 76. As seen in FIG. 1, the bottom of outer partition 82 is coplanar with main partition 40 and separates collection chamber 44 from connecting chamber 76.

As mentioned above, fluid communication into connecting chamber 76 is provided by passageway 74 through a semicircular opening 86 at the top of vertical partition 70. One-way fluid communication out of connecting chamber 76 is provided through a one-way outlet valve 88. A central orifice (not shown) and four peripheral orifices (not shown) extend through the bottom of inner partition 80. Valve 88 has a stem that is mounted in the central orifice and an enlarged head that extends over the peripheral orifices. Thus, when pressure in underwater seal chamber 42, collection chamber 44, and connecting chamber 76 exceeds the pressure in outlet chamber 72, the head of valve 88 will be forced upwardly so as to permit the passage of gases into outlet chamber and equalize the pressures therebetween. However, when the pressure is higher within outlet chamber 72 than within the rest of drainage device 10, valve 88 will remain closed preventing fluid communication in the opposite direction.

As can be clearly seen in FIGS. 1 and 3, connecting chamber 76 provides an enclosed chamber from the end of tubular passageway 74 to the inlet of outlet chamber 72 and prevents direct communication between collection chamber 44 and valve 88. In this way, valve 88 is protected against contamination from liquids contained in collection chamber 44 which could cause malfunctioning of valve 88.

A positive pressure release valve 90 is physically located in the far corner of outlet chamber 72 in an enclosed area 92 (FIG. 3). Enclosed area 92 is formed by vertical partition 70, a further vertical plate 93 located between vertical partition 70 and second end wall 20, a vertical connecting plate 94 (FIG. 5) attached between vertical partition 70 and plate 93, and a bottom 96 having an orifice 98 therethrough (see FIG. 3). Two orifices 100 (FIG. 5) located in container top wall 22 provide fluid communication between enclosed area 92 and the outside atmosphere.

When drainage device 10 is used, it is normally used with a suction from a controlled suction device attached to container outlet 28. However, in some cases, drainage device 10 can also be used without a suction. In either case, drainage device 10 can be used without prefilling the fluid seal. A thoracotomy tube (not shown) is connected between the pleural cavity of the patient and container inlet 26. One-way outlet valve 88 protects the patient from the admission of atmospheric air with the resulting danger of pneumothorax. The liquid secretions from the pleural cavity initially fill cup portion 48 to provide an underwater seal at the lower end of inlet tube 38. When cup portion 48 is filled with liquid, the liquid overflows onto the top of main partition 40. Initially, accurate measurements of the liquid secretion can be made inside cup portion 48, which can be calibrated.

In the event suction is to be used, the hose from a regulated suction source is attached to outlet 28 and the desired degree of negativity may be maintained within the collection chamber and pleural cavity. When operated with suction, additional protection is provided against possible build up of positive pressure within the collection chamber and the pleural cavity of the patient by positive pressure release valve 90, which can open in the event of sudden high pressure surges within drainage device 10.

Container 12 is also provided with two recesses 110 and 112 in rear wall 16. As depicted in FIG. 1, recesses 110 and 112 extend upwardly from bottom wall 24 to a point approximately one-third of the way up rear wall 16. Recesses 110 and 112 act as guide elements and are adapted to receive a corresponding hanger element 114 that is shaped as depicted in FIG. 1 so as to provide a floor stand for drainage device 10 when it must be supported on a horizontal surface. There are further provided two hanger brackets 116 rigidly mounted near the top of first and second end walls 18 and 20 and provided with a series of supporting ledges 118. As is also depicted in FIG. 1, drainage device 10 can be hung from a bed rail, for example, with one end of hanger element 114 engaging one of bracket ledges 118 and the other end engaging the bed rail.

Also depicted in FIG. 1 located at the upper, second end of container 12 are two box-shaped channels 120. Channels 120 are used to engage corresponding members mounted on a separable suction control chamber for rigidly attaching the suction control chamber to drainage device 10. A separable suction control chamber is disclosed in our copending patent application Ser. No. 52,825 filed June 27, 1979, incorporated herein by reference. This separable suction control chamber is also provided with a needle mounted on the suction control chamber so as to puncture rubber diaphragm 36 of drainage device 10 when the two are attached. As explained in our above-mentioned patent application, the needle has a bore therein so that fluid communication can be obtained between the attachable suction control chamber and the underwater seal chamber 42 of the present drainage device 10.

In the use of drainage devices wherein the underwater seal is formed directly at the end of the thoracotomy tube by the liquid secretions from the pleural cavity of the patient, it is important that the drainage device be so constructed that excessive negativity within the pleural cavity, such as might be caused by blockage in the bronchial tubes or the like, cannot cause the fluid within the underwater seal to rise within the thoracotomy tube and pass back into the pleural cavity. This is precluded in the presently disclosed apparatus because of the incorporated one-way outflow valve. In addition, because of the U-shaped baffle 56 and the location of tubular passageway 74 at the upper end of baffle 56, means are provided to prevent the flow of fluid from the underwater seal chamber into the outlet chamber. Gate 58 blocking the entrance of fluid through opening 56 in main partition 40 together with the sloping of main partition 48 assure that a sufficient reservoir of liquid is maintained in seal chamber 42 to keep cup portion 48 full of liquid and the seal in tact in the event drainage device 10 is inadvertently tilted.

Obviously, many modifications and variations of the present invention are possible in light of the above teachings.

What we claim as new and is desired to be secured by Letters Patent is:

1. A drainage device comprising a closed container, an inlet to said container in the upper end thereof, a partition extending at least partially across said container to form a collection chamber beneath the partition and an underwater seal chamber above the partition, an outlet to atmosphere from said container, an outlet chamber formed within said container and surrounding said outlet to atmosphere, a discrete passageway extending above said partition in said underwater seal chamber and adjacent the upper end of said container to an inlet opening in said outlet chamber, oneway valve means disposed in said outlet chamber and in the path of fluid flow through the inlet to said outlet chamber and the outlet to atmosphere, an opening in said partition to permit flow of liquid from said underwater seal chamber to said collection chamber, and means in said underwater seal chamber for inhibiting the flow of liquid through said discrete passageway.

2. A drainage device according to claim 1 wherein said opening in the partition is located substantially centrally of the partition and said last named means comprises a substantially vertical baffle extending around the periphery of said opening.

3. A drainage device according to claim 1 wherein the last named means comprises a baffle extending from the partition to the top wall of the container around the periphery of the opening in said partition and including an opening therein to permit the flow of fluid therethrough from the underwater seal chamber into the collection chamber.

4. A drainage device according to claim 3 wherein said passageway opens into the underwater seal chamber at the upper end of said baffle.

5. A drainage device according to claim 1 and further including an inlet tube extending from said inlet into a U-shaped recessed portion in said partition.

6. A drainage device according to claim 5 wherein said partition is spaced a greater distance from the top wall of said container adjacent one end of the partition than at the opposite end of the partition.

7. A drainage device comprising a closed container having three chambers therein, said chambers comprising a collection chamber, an underwater seal chamber and an outlet chamber, said outlet chamber including an outlet to atmosphere, an inlet from the underwater seal chamber and a oneway valve disposed in the passageway between the inlet and outlet to the outlet chamber, a partition extending from the outlet chamber to the opposite end wall of the container forming the bottom wall for the underwater seal chamber, an opening in the partition forming a fluid passageway between the underwater seal chamber and the collection chamber, a thoracotomy tube inlet into said underwater seal chamber, and baffle means surrounding the opening in the partition to prevent substantial loss of fluid from the underwater seal chamber into the collection chamber when the container is tipped.

8. A drainage device according to claim 7 wherein said last named means comprises a baffle extending substantially vertically from the partition to the top wall of the container with one side of the baffle extending only a limited distance toward the top wall to permit fluid flow thereover from the underwater seal chamber to the collection chamber.

9. A drainage device according to claim 8 and further including a tubular passageway from the upper end of said baffle to the inlet to said outlet chamber.

10. A drainage device according to claim 7 and further including a U-shaped recess in said partition disposed immediately below the thoracotomy tube inlet and a tubular extension formed between said inlet and the recess.

11. A drainage device according to claim 9 and further including means providing an enclosed chamber from said tubular passageway to the inlet of said outlet chamber.

* * * * *